United States Patent [19]

Yoshino et al.

[11] 4,152,215
[45] May 1, 1979

[54] APPARATUS FOR CONTROLLING pH OF CULTURE SOLUTION FOR A LIVING ORGANISM

[75] Inventors: Yohzoh Yoshino, Hirakata; Hidehiko Kawabe, Moriguchi, both of Japan

[73] Assignee: Matsushita Electric Industrial Co., Ltd., Osaka, Japan

[21] Appl. No.: 851,583

[22] Filed: Nov. 14, 1977

[30] Foreign Application Priority Data

Nov. 12, 1976 [JP] Japan .............................. 51-136652

[51] Int. Cl.$^2$ ............................................. C12K 1/10
[52] U.S. Cl. ................................ 195/127; 204/180 P; 204/301; 47/62
[58] Field of Search ................... 195/127; 204/180 P, 204/301; 47/62

[56] References Cited

U.S. PATENT DOCUMENTS

| 2,739,934 | 3/1956 | Kunin | 204/180 P X |
| 3,671,412 | 6/1972 | Lohr | 204/301 X |
| 3,989,613 | 11/1976 | Gritzner | 204/180 P X |
| 4,043,895 | 8/1977 | Gritzner | 204/301 |
| 4,049,519 | 9/1977 | Sloan | 204/301 X |
| 4,057,483 | 11/1977 | Giuffrida | 204/301 |
| 4,070,263 | 1/1978 | Treille et al. | 204/301 X |

Primary Examiner—Raymond N. Jones
Assistant Examiner—Robert J. Warden
Attorney, Agent, or Firm—Wenderoth, Lind & Ponack

[57] ABSTRACT

Electrolysis is employed for raising or reducing pH of culture solution. Electrolyte contained in a vessel having at least one ion exchange membrane as a wall is provided so as to confront the culture solution, with the ion exchange membrane lying therebetween. Electrodes are provided both in the electrolyte and the culture solution. With these electrodes the electrolysis is carried out through the ion exchange membrane. Thus formed alkali or acid changes the pH of the culture solution. By controlling the time or supplied current for the electrolysis, required pH can be accurately obtained.

4 Claims, 7 Drawing Figures

APPARATUS FOR CONTROLLING PH OF CULTURE SOLUTION FOR A LIVING ORGANISM

BACKGROUND OF THE INVENTION

The present invention relates to a method of and an apparatus for controlling the pH of culture solution for a living organism.

It is quite important to control pH in the culture of a living organism such as in hydroponics. Such method has hitherto been used as neutralizing by adding alkali or acid into a culture solution tank from storage tanks. The amount of alkali or acid to be added is based on the measurement with a pH meter. When automatic control is required, the storage tanks for alkali and acid are provided with electrovalves which control the release of the contents, and the electrovalves are driven by a controller which works responsively to the signal from the pH meter having an electrode inserted into the culture solution.

Such method, however, has not been satisfactory for reasons as follows:

A desirable value of a pH of the culture solution is in a narrow range near neutrality. Therefore when concentrated alkali and acid is used, it is difficult to maintain pH in the desirable range because pouring thereof easily causes large change of pH. To accurately control a pH, it is desirable to use dilute alkali and acid. The use of dilute alkali and acid requires large tanks for storing them. Further it is necessary to supplement alkali or acid in the storage tanks frequently. Further the electrovalves for the tanks must be corrosion-resistant because alkali or acid flows therethrough. Further, the case possibly occurs that alkali solution reacts with $CO_2$ gas in air to make carbonate, and it enters into the culture solution through neutralization, resulting in bad effect on plants, or it chokes up the gateway by solidifying.

SUMMARY OF THE INVENTION

It is an object of the invention to provide a method of controlling the pH of culture solution whereby such control can be performed at high accuracy.

It is a further object of the invention to provide an apparatus for such pH-control having a simple and compact construction.

According to the present invention, electrolysis through an ion exchange membrane is employed. A vessel having a partition wall of an ion exchange membrane is provided in the manner such that the culture solution abuts on the ion exchange membrane from outside of the vessel. Within the vessel is held electrolyte of inorganic ions. Electrodes are provided on both sides of the ion exchange membrane, i.e. both in the culture solution and the electrolyte. With these electrodes electrolysis is performed through the ion exchange membrane.

As the result of the electrolysis, formed alkali or acid changes a pH of the culture solution. By controlling the time and supplied current of the electrolysis, required pH can easily be obtained.

DETAILED DESCRIPTION OF THE INVENTION

Figure 1:
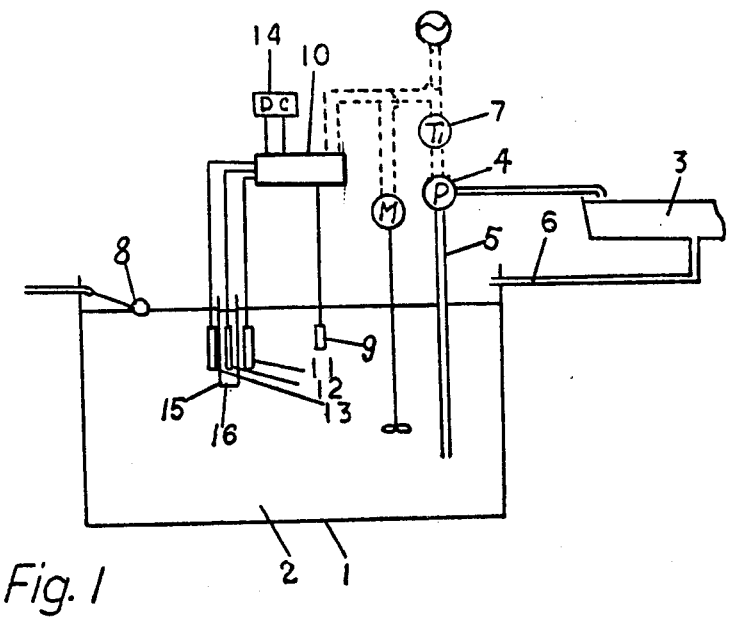
FIG. 1 is a schematic sectional view for explaining an automatic pH controlling method for culture solution embodying the present invention.

FIG. 1 illustrates a pH controlling apparatus which is used in a hydroponics system. A culture solution tank 1 is provided for storing culture solution 2. The culture solution 2 is conveyed to a growing vessel 3 by a pump 4. It is pumped up through a supply pipe 5 and returns from the growing vessel 3 to the culture solution tank 1 through a drain pipe 6. The operation of the pump 4 is controlled by a timer 7 so as to be driven intermittently. As the case may be the pump 4 is driven continuously. The level of the culture solution is maintained constant by a constant-level regulator 8. The pH of the culture solution 2 is measured by a pH electrode 9 and obtained data signal is transmitted to a controller 10. The controller 10 is connected with electrodes 11, 12 and 13 for electrolysis and a DC power source 14, and controls the supplying of current from the DC power source 14 to the electrodes 11, 12 and 13. Such control is made in accordance with the result of collation between the pH measured by the pH electrode 9 and a required range of pH preset in the controller 10. When the measured value is out of the preset range, the DC current from the DC power source 14 is supplied between the electrodes 11 and 12 or the electrodes 12 and 13, whereby the electrolysis occurs so as to maintain the pH of culture solution 2 in the preset range. The electrode 12 is placed within an electrolyzing vessel 15 in which an electrolyte 16 is held.

Figure 2:
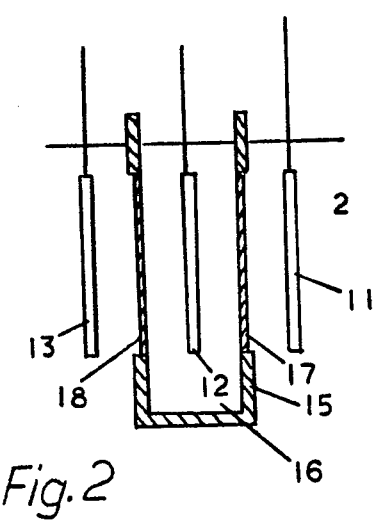
FIG. 2 is a sectional view illustrating an important part of a pH controlling apparatus illustrated in FIG. 1.

As illustrated in FIG. 2, the electrolyzing vessel 15 is box-shaped and two opposed walls thereof are partially constructed by ion exchange membranes 17 and 18. In this embodiment, the membrane 17 is a cation exchange membrane and the membrane 18 an anion exchange membrane. The electrodes 11 and 12 confront each other, with the cation exchange membrane 17 lying therebetween. And the electrodes 12 and 13 confront each other, with the anion exchange membrane 18 lying therebetween. As the electrolyte 16, for example, $K_2SO_4$ aqueous solution is used. The electrodes 11, 12 and 13 may be of platinum.

Figure 3:
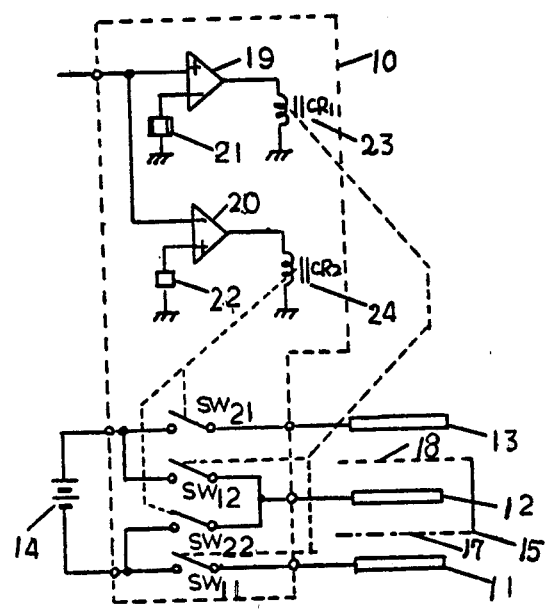
FIG. 3 is a circuit diagram of the pH controlling apparatus illustrated in FIG. 1.

The controller is, for example, constructed as illustrated in FIG. 3. A pH signal voltage from the pH electrode 9 is supplied to the comparators 19 and 20. Reference voltages for the comparators 19 and 20 are supplied from variable voltage sources 21 and 22, respectively. The variable voltage source 21 is preset correspondingly to the lower limit of the required pH range and the variable voltage source 22 to the upper limit. The coupling between the comparators 19 and 20 and the input signals are in such relation that the comparator 19 generates an output signal if the pH signal voltage is lower than the reference voltage of the variable voltage source 21 and the comparator 20 generates an output signal if the pH signal voltage is higher than the reference voltage of the variable voltage source 22. The outputs of the comparators 19 and 20 are coupled to relays $CR_1$ 23 and $CR_2$ 24, respectively. The electrode 11 is connected with the negative terminal of the DC power source 14 through a contact $SW_{11}$ which is one of the contacts of the relay $CR_1$ 23. The electrode 13 is connected with the positive terminal of the DC power source 14 through a contact $SW_{21}$ which is one of the contacts of the relay $CR_2$ 24. The electrode 12 is connected with the positive terminal of the DC power source 14 through another contact $SW_{12}$ of the relay $CR_1$ 23, and with the negative terminal of the DC power source 14 through another contact $SW_{22}$ of the relay $CR_2$ 24.

Thus when the pH signal voltage is lower than the preset range, i.e. lower than the reference voltage of the variable voltage source 21, the relay $CR_1$ 23 is driven by the output of the comparator 19 and the contacts $SW_{11}$ and $SW_{12}$ are made. Thereby electrolysis through the cation exchange membrane 17 is carried out by the current supplied from the DC power source 14, with the electrode 12 as the anode and the electrode 11 as the cathode.

The reaction in the electrolyzing vessel 15 is represented as follows:

$$2K^+ + SO_4^{2-} + 2H_2O \rightarrow 1/2 O_2 \uparrow + 2H^{+\cdot} + SO_4^{2-} + 2e$$

The $K^+$ ions are transferred by migration to the side of the electrode 11 through the cation exchange membrane 17.

On the other hand, the reaction in the culture solution 2 is as follows:

$$2H_2O + 2e \rightarrow H_2 \uparrow + 2OH^- + 2K^+$$

The $OH^-$ ions thus generated on the electrode 11 raise the pH of the culture solution 2. The electro neutrality in the culture solution 2 is maintained by the $K^+$ ions transferred from the electrolyte 16 by the amount corresponding to electrical quantity for the electrolysis.

Thus the pH of the culture solution is raised to within the required range.

When the pH signal voltage is higher than the preset range, i.e. higher than the reference voltage of the variable voltage source 22, the relay $CR_2$ 24 is driven by the output of the comparator 20 and the contacts $SW_{21}$ and $SW_{22}$ are made. Thereby electrolysis through the anion exchange membrane 18 is carried out, with the electrode 13 as the anode and the electrode 12 as the cathode.

The reactions thereof are as follows:

Anode: $2H_2O \rightarrow 2H^+ + SO_4^{2-} + 1/2 O_2 \uparrow + 2e$

Cathode:
$2H_2O + 2K^+ + SO_4^{2-} + 2e \rightarrow H_2 \uparrow - + 2OH^- + 2K^+$ Thus in the culture solution 2 wherein the anodic reaction occurs, the concentration of $H^+$ ion increases accordingly as the electrolysis progresses, and the pH falls.

Although $K_2SO_4$ aqueous solution is used as the electrolyte 16 in the above-mentioned embodiment, other material may be used. It is preferable that the electrolyte 16 not have a bad effect on plants because the ions within the electrolyzing vessel 15 are transferred to the culture solution 2 through the ion exchange membranes 17 and 18. Examples of satisfactory materials result from combination between $K^+$, $NH_4^+$, $Ca^{++}$, $Mg^{++}$, $NO_3^-$, $SO_4^{2-}$ and $PO_4^{3-}$ which are the ions contained in the culture solution 2 in substantial amounts.

Figure 4:
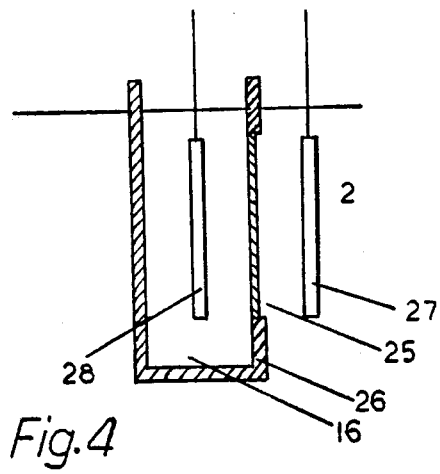
FIGS. 4 and 5 are sectional views illustrating other embodiments of such part of the pH controlling apparatus as illustrated in FIG. 2.

The electrolysis may be carried out by the use of two electrodes and one ion exchange membrane. As illustrated in FIG. 4, for example, an anion exchange membrane 25 is employed and formed as one partition wall of an electrolyzing vessel 26. Electrodes 27 and 28 confront each other, with the anion exchange membrane 25 lying therebetween.

If the pH of the culture solution should be raised, the electrode 28 in the vessel 26 is used as an anode and the electrode 27 as an cathode. The reactions in such case are as follows:

Anode: $H_2O + 2K^+ + SO_4^{2-} \longrightarrow$
$\frac{1}{2}O_2 + 2H^+ + 2K^+ + SO_4^{2-} + 2X^- + 2e$
(migration)

Cathode: $2H_2 + 2e + 2M^+ + 2X^- \longrightarrow$
(migration)
$H_2 + 2OH^- + 2M^+$ where the $X^-$ and $M^+$ represent ions contained in the culture solution 2, as fertilizer such as $K^+$, $NH_4^+$, $NO_3^-$, etc. These ions may be a multi valent ion such as $Ca^{++}$, $Mg^{++}$, $PO_4^{3-}$, $SO_4^{2-}$, etc..

If the pH of the culture solution should be lowered, the electrodes 27 and 28 are used with polarities the reverse of the above case. The reactions are as follows:

Cathode:
$2H_2O + K^+ + SO_4^{2-} + 2e \rightarrow H_2 + 2OH^- + K^+$

Anode:
$H_2O + 2M^+ + 2X^- \rightarrow \frac{1}{2}O_2 + 2H^+ + 2X^- + SO_4^{2-}$ Instead of the anion exchange membrane 25, a cation exchange membrane can be used for constructing the system in the similar manner.

Figure 5:
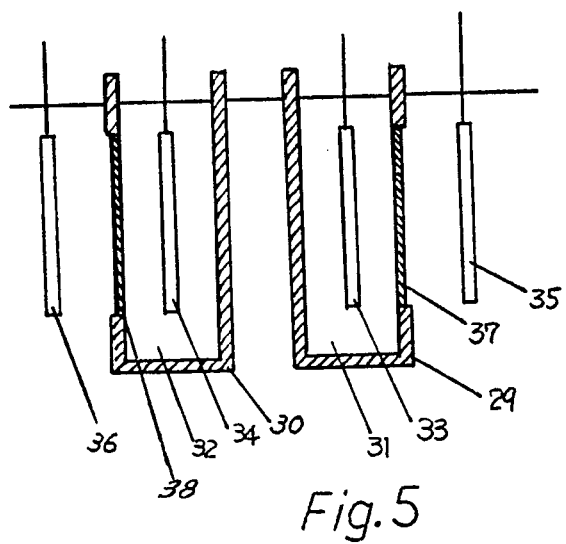

Furthermore, pH of the culture solution may be also controlled by an apparatus as shown in FIG. 5. This apparatus has two electrolyzing vessels 29 and 30 which respectively contain electrolyte 31 and electrolyte 32, two electrodes 33 and 34 which are respectively immersed in the electrolyte 31 and electrolyte 32, and two electrodes 35 and 36 immersed in the culture solution 2. This apparatus is particularly available for the case where ion-species of cations and anions, which respectively migrate from electrolyte 31 and electrolyte 32 to the culture solution 2, have to be restricted for some reason and the compounds composed of these ions show poor solubility. For example, if cations are to be restricted to $Ca^{++}$ and anions to $SO_4^{2-}$, $CaSO_4$ is produced as a compound of these ions. This compound shows poor solubility of the order of 2g/l and thereby it becomes difficult to allow the electrolyte to have a sufficient conductivity for causing satisfactory electrolysis. In this case, where the construction as shown in FIG. 5 is employed, an exchange membrane 37 provided at a portion of the electrolyzing vessel 29 is composed of a cation exchange membrane, the electrolyte 31 contains $Ca(NO_3)_2$ $4H_2O$ solution with a high solubility, and where the electrodes 33 and 35 provided on either side of the exchange membrane 37 are respectively used as an anode and a cathode, it is possible to permit $Ca^{++}$ cations in the electrolyte 31 to migrate into the culture solution 2 by electrolysis. On the other hand, where an exchange membrane 38 provided at a portion of the electrolyzing vessel 30 is composed of anion exchange membrane, the electrolyte 32 contains $K_2SO_4$ solution, and where the electrodes 34 and 36 provided on either side of the exchange membrane 38 are respectively used as a cathode and an anode, it is possible to permit $SO_4^{2-}$ anions in the electrolyte 32 to migrate into the culture solution by electrolysis.

In order to make the culture solution pH controlling apparatus miniaturize in size and light in weight, it becomes necessary to make the amount of the electrolyte 16 in the electrolyzing vessel 15 less as compared with that of the culture solution. However, when pH of the culture solution 2 is rectified by electrolysis, pH of the electrolyte 16 changes to the adverse direction with respect to the pH rectifying direction of the culture solution and this pH change of the electrolyte becomes larger with the decreasing of the amount of the electrolyte. Therefore, in order to restrict the pH change of the electrolyte 16 to as small as possible, it is preferable that the electrolyte 33 includes, as components, weak acid or weak base ion with a large buffer capacity, for example $H_2PO_4^-$, $HPO_4^{2-}$, $Ca^{++}$, $Mg^{++}$ or mixture thereof, among the combinations of a large number of ions included as fertilizers in the culture solution 2.

Furthermore, in FIGS. 2 and 3, if the ion exchange membrane 17 is composed of an anion exchange membrane, the ion exchange membrane 18 a cation exchange membrane, and like operation as described above is performed, namely, if electrolysis is caused by arranging, as an anode, the electrode 12 in the electrolyzing vessel 15 and, as a cathode, the electrode 11 in the culture solution 2 in a manner that they are positioned on either side of anion exchange membrane 17 or by arranging, as an anode, the electrode 13 in the culture solution 2 and, as a cathode, the electrode 12 in the electrolyzing vessel 15 in a manner that they are positioned on either side of the cation exchange membrane 18, ions in the culture solution 2 migrate into the electrolyzing vessel 15 through the ion exchange membranes 17 and 18, and thereby pH of the culture solution 2 may be controlled with maintenance of electro neutrality of the culture solution 2 and the electrolyte 16. In this case, because components included in the electrolyte 16 are never carried into the culture solution 2 by the electro-migration, it is unnecessary to pay attention to whether the components to be added in the electrolyte 16 adversely affect living organisms, and therefore they may be optionally selected. Thus, it becomes possible to add to the electrolyte 16 neutral salts with a high equivalent conductivity such as $KClO_4$, $K_4Fe(CN)_6$, $K_3Fe(CN)_6$, KI or the like, other than the combination of ions included as fertilizer components in the culture solution 2, and moreover it becomes also possible to add to the electrolyte 16 materials which give a large pH-buffer-capacity to the electrolyte, for example the material such as $MH_3(C_2O_4)_2 2H_2O$, $C_6H_4(COOM)COOH)$, $MH_2PO_4$, $M_2HPO_4$, $M_2HPO_4$, $M_2B_4O_7$, $MHCO_3$, $M_2CO_3$ or the mixture thereof wherein M denotes an alkaline metal such as K, Na, Li, or the like. Furthermore, if there is employed such a construction that ions emigrate only from the culture solution 2 into the electrolyzing vessel 15 by electrolysis, it becomes unnecessary to restrict the electrode reaction on the electrode 12 to water decomposition which generates $H^-$ and $OH^-$. Rather, in order to avoid a large pH-variation of the electrolyte 16, the electrolyte 16 and the electrode 12 may be composed of a material which permits the reaction which occurs prior to an $O_2$ evolution reaction as an anode reaction and prior to $H_2$ evolution as a cathode reaction; that is a dissolution-decomposition-reaction of Cu and Ag or a dissolution-deposition-reaction of Pb, Ni or Sn which occurs, due to a hydrogen overvoltage, prior to charge-discharge of $H_2$; or an oxidation-reduction reaction of ions such as

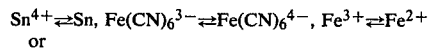

or the like. For example, in the event that Cu and $CuSO_4$ solution are respectively employed as the electrode 13 and the electrolyte 16, if the electrode 13 is used as an anode, an anode process becomes as follows:

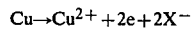

wherein $2X^-$ emigrates from the culture solution, and if the electrode 13 is used as a cathode, a cathode process becomes as follows:

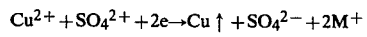

wherein $2M^+$ emigrates from the culture solution, whereby pH of the electrolyte in the electrolyzing vessel 15 substantially does not change.

In such arrangement, the material of the electrode 12 in the electrolyzing vessel 15 should be selected by considering the composition of the electrolyte 16. Namely, if it is desired to produce a dissolution-deposition reaction by employing the electrolyte including a salt such as $CuSO_4$, $AgNO_3$, $NiCl_2$ or $(CH_3COO)_2Pb$, the electrode material should be composed of Cu, Ag, Ni or Pb and if it is desired to produce an oxidation-reduction reaction of ions or a water decomposition by employing the electrolyte which includes mixed solution of $SnCl_2$-$SnCl_4$, $FeSO_4$-$Fe(SO_4)_3$ or $K_4Fe(CN)_6$-$K_3Fe(CN)_6$, the electrode material should be composed of a material being very or relatively stable in a range of 3-10 pH, for example Pt, Au, Carbon, stainless steel or Ni.

Furthermore, the electrolyzing apparatus for controlling pH of the culture solution may be set not only in the culture solution tank 1 as shown in FIG. 1, but also in the culture supplying tube 5, the growing vessel 3 or the draining tube 6. If the culture solution 2 is circulated, it may be set in any portion other than the portions as described above.

Figure 6:
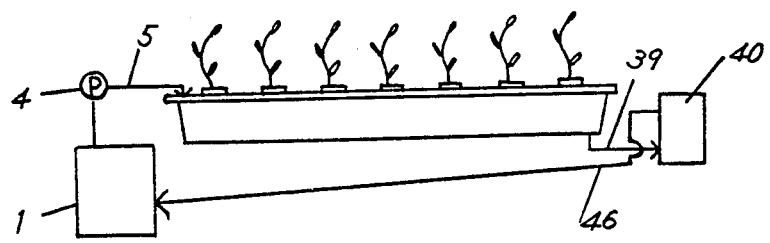
FIG. 6 is a schematic diagram illustrating another embodiment of the invention.
Figure 7:
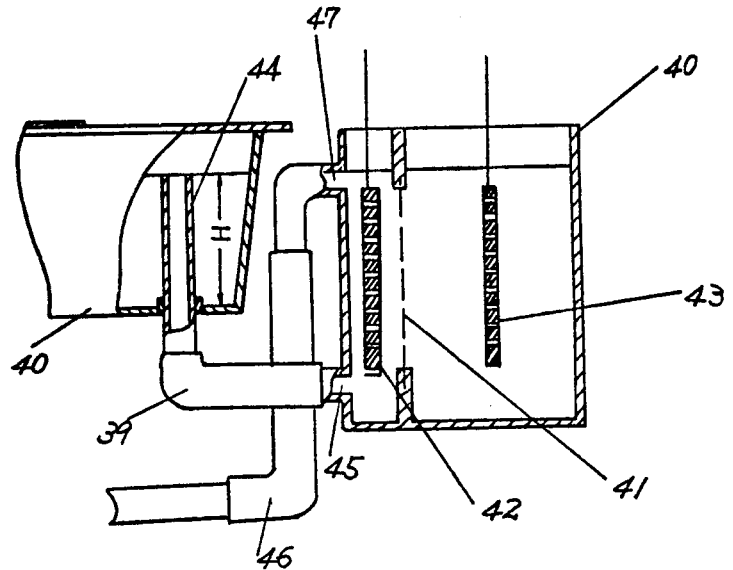
FIG. 7 is an elevational view partly in section of a part of the apparatus illustrated in FIG. 6.

In FIGS. 6 and 7, there is shown a pH controlling system for controlling pH of the culture solution wherein the electrolyzing device is placed at the end of a draining tube 39 with the culture solution being circulated. The electrolyzing vessel 40 of the electrolyzing device has therein an ion exchange membrane 41 and a pair of electrodes 42 and 43. In this system, when the depth of the culture solution 2 exceeds the height (H) of a water level controlling tube 44 for controlling the level of the culture solution to a constant level, the culture solution overflows into the electrolyzing vessel 40 through the inside of the level controlling tube 44, the draining tube 39 and an inlet 45 of the electrolyzing vessel 40, which inlet 45 is below the lower edge of the electrode 42, and thereafter it flows into a tube 46 through a space between the electrode 42 and the ion exchange membrane 41 and through an outlet 47 of the electrolyzing vessel 40, which outlet 47 is above the upper edge of the electrode 42. If the outlet 47 is below the upper level of the water level controlling tube 44, the culture solution in the electrolyzing vessel 40 keeps its level equal to the upper level of the water level controlling tube 44, thereby preventing the ion exchange membrane 41 from being damaged due to its drying. Furthermore, this system is effective in that an eduction of insoluble matter such as $Ca(OH)_2$, $Mg(OH)_2$ or the like, on the electrode 42 or on the exchange membrane 41 may be avoided because the culture solution is churned at the vicinity of the electrode 42 and the exchange membrane 41 by the circulation of the culture solution, which $Ca(OH)_2$ and $Mg(OH)_2$ is formed when $Ca^{++}$ and $Mg^{++}$ in the culture solution combine with $OH^-$ produced by electrolysis.

In the system as described above, it has a capacity to form in the culture solution by the electrolysis for 1 Hr, for example, an amount of an acid which is nearly equal to that in the case where 36 $N-H_2SO_4$ of about 1 ml is added to the culture solution. Since it is possible to decrease an electric current and to shorten a period of electrolysis, the electrolyzing apparatus of the present invention is available for a very accurate pH control and for a pH control which requires a slow pH change such as for a living organism which should not be subjected to an abrupt change of pH in a neutralization range of solution.

What we claim is:

1. An apparatus for controlling the pH of a culture solution for a living organism, which comprises: a culture solution vessel containing a culture solution; a pH electrode immersed in the culture solution for measuring the pH of the culture solution and for producing a signal in accordance with the pH measured; an electrolyte vessel immersed in the culture solution, the electrolyte vessel containing electrolyte therein and at least a portion of the wall of the electrolyte vessel being composed of an ion exchange membrane so that said ion exchange membrane is in contact with the culture solution; a first electrolysis electrode immersed in said electrolyte; a second electrolysis electrode immersed in the culture solution in a manner such that said ion exchange membrane is positioned between said first and second electrolysis electrodes; a DC voltage applying means for applying a DC voltage between said first and second electrolysis electrodes; and a pH controller that activates the DC voltage applying means in accordance with the signal produced by the pH electrode.

2. An apparatus according to claim 1, wherein a further portion of the wall of the electrolyte vessel is composed of a second ion exchange membrane, and a third electrolysis electrode is immersed in the culture solution in a manner such that said second ion exchange membrane is positioned between said first and third electrolysis electrodes.

3. An apparatus according to claim 1, further comprising: a second electrolyte vessel which contains electrolyte, a portion of the wall of said second electrolyte vessel being composed of an anion exchange membrane; a third electrolysis electrode immersed in the electrolyte contained in said second electrolyte vessel; a fourth electrolysis electrode immersed in the culture solution in a manner such that said anion exchange membrane is positioned between said third and fourth electrolysis electrodes; and wherein said ion exchange membrane is composed of a cation exchange membrane, said first and second electrolysis electrodes are respectively used as an anode and a cathode, and wherein said third and fourth electrolysis electrodes are respectively used as a cathode and an anode.

4. An apparatus according to claim 1, wherein said culture solution is circulated so that eduction of insoluble matters on said ion exchange membrane and on said second electrolysis electrode is avoided.

* * * * *